United States Patent
Mottola et al.

[19]

[11] Patent Number: 6,059,759
[45] Date of Patent: May 9, 2000

[54] INFUSION CATHETER SYSTEMS WITH TACTILE SENSING FEEDBACK

[75] Inventors: Jim D. Mottola, South Jordan, Utah; Joseph E. Biche, Mayfield, N.Y.; Stephen W. Carlstrom, Salt Lake City; Darwin L. Mullins, Kearns, both of Utah

[73] Assignee: Merit Medical Systems, Inc., South Jordan, Utah

[21] Appl. No.: 08/949,977

[22] Filed: Oct. 14, 1997

[51] Int. Cl.[7] .................................................. A61M 25/00
[52] U.S. Cl. .......................... 604/264; 604/523; 604/528; 604/533
[58] Field of Search .................................... 604/264, 523, 604/528, 533, 534, 538, 95, 96, 500, 507, 508

[56] References Cited

U.S. PATENT DOCUMENTS

| | | | |
|---|---|---|---|
| 5,021,044 | 6/1991 | Sharkawy | 604/528 X |
| 5,184,627 | 2/1993 | de Toledo | 604/264 X |
| 5,226,423 | 7/1993 | Tenerz et al. | 604/528 X |
| 5,409,470 | 4/1995 | McIntyre et al. | 604/528 |
| 5,447,503 | 9/1995 | Miller | 604/528 |
| 5,591,137 | 1/1997 | Stevens | 604/256 |
| 5,868,685 | 2/1999 | Powell et al. | 604/528 X |

*Primary Examiner*—John D. Yasko
*Attorney, Agent, or Firm*—Workman, Nydegger & Seeley

[57] ABSTRACT

A catheter system including an infusion catheter interacting with an occluding wire. The infusion catheter has an interior surface defining a lumen longitudinally extending between a proximal end and a distal end. The interior surface of the catheter includes a cylindrical first portion positioned at the proximal end, a cylindrical second portion positioned at the distal end, and an annular, sloped, tapered portion extending therebetween. The second portion terminates at a tip opening. An annular sensing ridge radially inwardly projecting around the tip opening. A plurality of small infusion holes extend through the side of the infusion catheter proximal of the tapered portion. The occluding wire includes a thin placement wire having an enlarged occluding ball placed at the distal end thereof. Projecting from the occluding ball on the side opposite the positioning wire is a coiled spring wire. The spring wire has ridges formed by the top of the wire and grooves formed between each coil. The maximum outer diameter of the spring wire is larger than the inner diameter of the annular sensing ridge. Accordingly, as the coiled spring wire passes through the sensing ridge, the sensing ridge tactually engages the coiled wire to causes vibrations felt by the user.

22 Claims, 12 Drawing Sheets

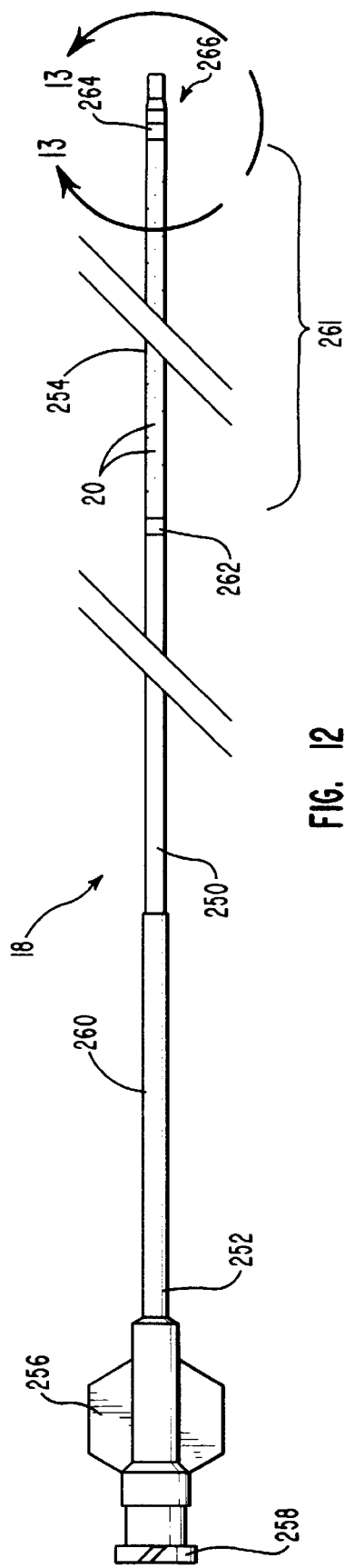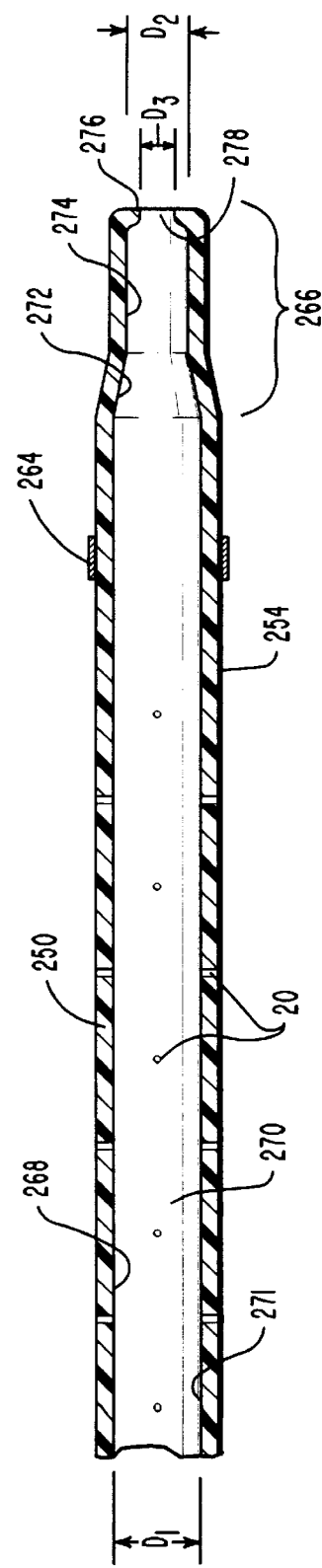
FIG. 12
FIG. 13

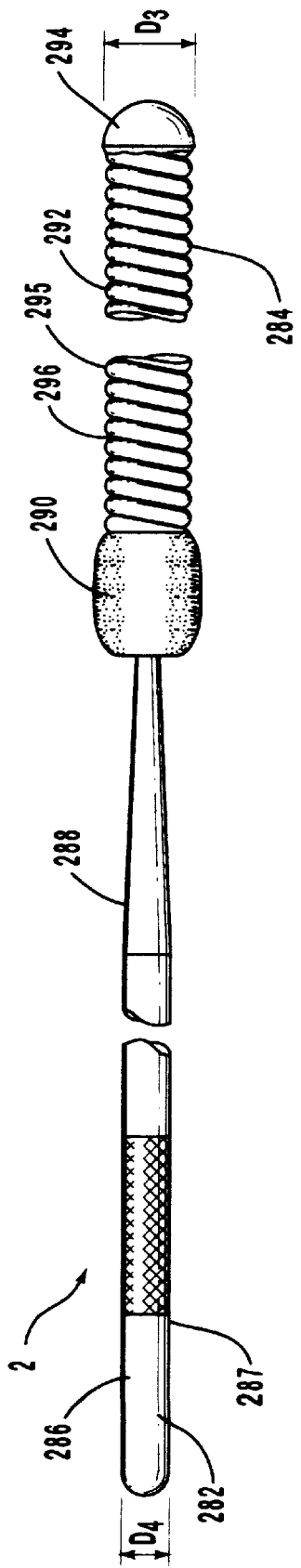
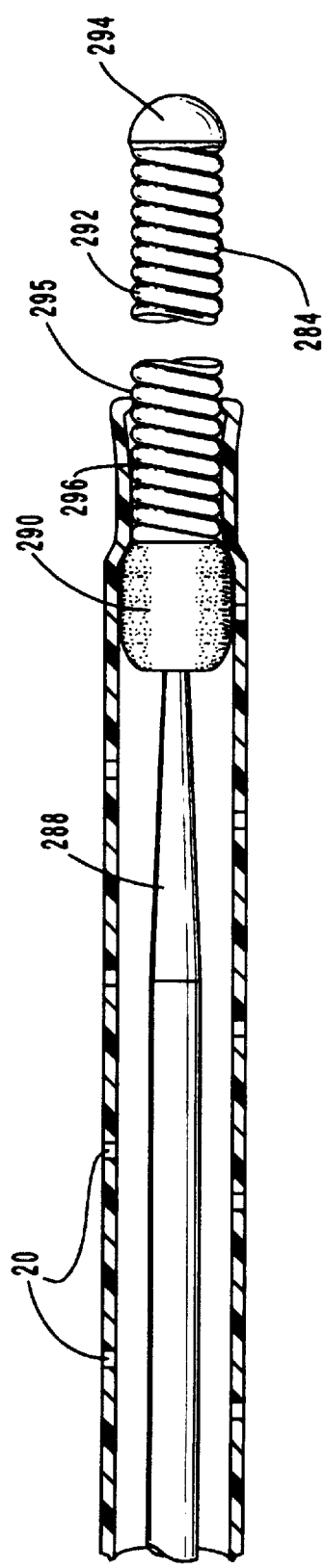
FIG. 14
FIG. 15

INFUSION CATHETER SYSTEMS WITH TACTILE SENSING FEEDBACK

BACKGROUND OF THE INVENTION

1. Field of the Invention

The present invention relates to catheter systems and, more specifically, infusion catheters having a tip opening and an occluding wire configured to selectively seal the tip opening closed.

2. The Relevant Technology

A reasonably common and dangerous medical condition arises when a blood clot develops in the vascular system of the body of a patient. A blood clot or thrombus can endanger the health of a patient in at least two significant ways. First, the clot may restrict or even completely stop essential blood flow to a portion of the patient's body. If the blood flow to the brain or heart for example is restricted the patient's life may be placed in jeopardy. Additionally, a clot may break loose from the site at which it formed and be carried by the blood stream to an organ, such as the heart, where it may cause irreparable damage or even death. Accordingly, when a blood clot is detected, it must be quickly and effectively treated.

One method involves surgery to remove the clot and repair the blood vessel. A less invasive method uses thrombolytic drugs to break up, or lyse, the thrombus. This method of treating a blood clot consists of inserting a catheter into the patient's vascular system, preferably near the site of the clot. If the catheter enters the vascular system near the clot, the catheter alone may be used. If, for a variety of reasons, the catheter must be inserted into the vascular system at a distance from the clot, placement of the catheter may be aided by using a guide wire or introducer sheath, which can be used to push and guide the catheter through the vessels or arteries of the vascular system to reach the clot.

Once the catheter is positioned at the site of the clot, a thrombolytic fluid capable of dissolving the clot, such as urokinase or streptokinase, is delivered to the site of the clot by means of the catheter. Conventional catheters have a lumen, i.e., an internal passage, that allows the thrombolytic fluid to flow through the catheter to one or more discharge openings at or near the distal end of the catheter. The discharged thrombolytic fluid then dissolves or lyses the clot, thus removing the danger to the patient.

Not all clots are easily or successfully lysed. Some clots form around arterial lesions, which clots may not be easily lysed or broken up by the thrombolytic fluid and which usually require surgical removal. Additionally, some clots may be extremely thick, extending for a relatively long distance through a blood vessel of the circulatory system. Such a thick clot may require considerable amounts of time and heavy irrigation of thrombolytic fluid to dissolve.

Typically, a guide wire is used in conjunction with a catheter to facilitate placement of the catheter. The guide wire can also serve to penetrate the clot in order to form a passage therethrough so that the catheter can be inserted within the interior of the clot. This helps to ensure that the thrombolytic fluid is concentrated or focused at the location of the clot, since excessive thrombolytic fluid in the bloodstream can have adverse effects on the patient.

After the guide wire has been used to create a narrow passage through the clot, particularly a thick clot, the thrombolytic fluid is released through the one or more openings within the catheter. In the beginning stages of thrombolytic therapy, thrombolysis was carried out using a catheter with a single opening at the distal end of the catheter. Methods employing a simple catheter required movement of the catheter from one end of the clot to the other while dispensing the thrombolytic fluid in order to adequately distribute the fluid over the entire length of the thrombus.

Subsequent attempts have been made to improve the dissolution of blood clots by forcefully injecting a dissolving agent simultaneously along the length of the blood clot. In one such approach, the catheter has a large tip opening and a plurality of small side opening positioned at the distal end of the catheter. The tip opening is used for placement of the catheter. Initially, a long thin guide wire is slid into the vascular system such that the distal end of the guide wire extends through the blood clot. Next, the end of the guide wire outside the body of the patient is received within the tip opening of the catheter. The catheter is then slid over the guide wire, while holding the guide wire stationary, until the infusion holes in the catheter are positioned within the blood clot. Once the catheter is positioned, the guide wire is removed while holding the catheter stationary.

To force the dissolving agent to pass through the infusion holes in the catheter, it is first necessary to block or occlude the large tip opening. This is accomplished by inserting a thin placement wire having an enlarged occluding ball at the distal end thereof into the end of the catheter outside of the patient. The placement wire is advanced until the occluding ball is sealingly disposed at the tip opening. With the placement wire still inside the catheter, the proximal end of the catheter is fluid coupled with a pumping system for injecting the dissolving agent into the catheter and out through the infusion holes thereof. Sufficient dissolving agent is forcefully pumped through the catheter and out against the clot to dissolve the clot.

Although useful, there are several shortcomings associated with the above described catheter system. Most notably, since the catheter tip is located within the body of the patient, it is difficult for the surgeon to determine when the occluding ball of the placement wire is approaching the catheter tip. Although the tip is slightly tapered for seating of the occluding ball, if the surgeon pushes too hard on the occluding wire, the occluding ball can be pushed through the tip opening. If this happens, the catheter and placement wire must be removed and the process of placement repeated.

OBJECTS AND BRIEF SUMMARY OF THE INVENTION

Accordingly, it is an object of the present invention to provide improved infusion catheter systems.

Another object of the present invention is to provide improved infusion catheter systems where a surgeon can tactually feel when the occluding ball on the positioning wire is approaching the tip opening of the catheter.

To achieve the foregoing objects, and in accordance with the invention as embodied and broadly described herein, an infusion catheter system is provided. The system includes an infusion catheter interacting with an occluding wire.

The infusion catheter has an interior surface defining a lumen longitudinally extending between a proximal end and a distal end. The proximal end of the catheter is fluid coupled to a pump. The interior surface of the catheter includes a cylindrical first portion positioned at the proximal end, a cylindrical second portion positioned at the distal end, and an annular, sloped, tapered portion extending therebetween. The second portion terminates at a tip opening. An annular sensing ridge radially inwardly projects around the tip opening. A plurality of small infusion holes extend through the side of the infusion catheter proximal of the tapered portion.

The infusion catheter is preferably placed by first inserting a guide wire into the vascular system of the body of a patient. With the guide wire appropriately positioned, the infusion catheter is slid over the exposed end of the guide wire and fed to the distal end positioned within the vascular system. The guide wire is then removed such that the infusion catheter remains in the vascular system. The pump is then coupled to the proximal end of the infusion catheter by way of a hemostasis valve.

Prior to pumping fluid into the infusion catheter, the tip opening is first blocked or occluded. This is accomplished by advancing an occluding wire into the lumen of the catheter. The occluding wire includes a thin placement wire having an enlarged occluding ball placed at the distal end thereof. Projecting from the occluding ball on the side opposite the positioning wire is a coiled spring wire. The spring wire has ridges formed by the top of the wire and grooves formed between each coil. The maximum outer diameter of the spring wire is larger than the inner diameter of the annular sensing ridge. Accordingly, as the coiled spring wire passes through the sensing ridge, the sensing ridge vibrates over the coiled wire. These vibrations can be tactually felt by the surgeon through the occluding wire and the catheter. These vibrations provide notice to the surgeon that the occluding ball is close to the tapered portion. The surgeon can then carefully advance the occluding wire until the occluding ball seats and seals against the tapered portion. In this position, fluid can be pumped into the catheter and out through the infusion holes.

The inventive catheter system provides a unique advantages over prior art systems. Specifically, as a result of the vibrational interaction between the sensing ridge and the spring wire, the surgeon is notified of the relative position of the occluding ball. The surgeon can then carefully advance the occluding wire to prevent pushing the occluding ball through the tip opening.

Although the sensing ridge is disclosed herein as being formed on an infusion catheter, this embodiment is merely illustrative and in no way limiting. The sensing ridge could be placed on a variety of different types and styles of catheters to enable a surgeon to tactually feel the relative position of a wire positioned within the catheter. For example, the sensing ridge could be positioned at the tip opening of a conventional catheter that has no infusion holes.

The spring wire is preferably positioned at the tip of the occluding wire although it could be positioned anywhere along the usable length of the occluding wire so long as it provided the inventive tactual sensing function. The surgeon could then determine when the occluding wire is projecting through the tip opening in the catheter.

In a preferred embodiment, the spring coil portion of the inventive occluding wire will be larger in diameter than the conventional wire portion such that the conventional wire portion does not itself sense and/or such that the sensing ability of the tactual portion is not diminished or otherwise compromised.

In addition to the aforementioned use, the sensing spring wire can be connected to other wires used in surgery, such as a guide wire, for use in positioning such other wires within, e.g., balloon catheters, guiding catheters, or in conjunction with any intravascular wires or catheters.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIG. 12 is a side view of the infusion catheter shown in FIG. 1;

FIG. 13 is a cross-sectional side view of the distal end of the catheter shown in FIG. 12;

FIG. 14 is a side view of the occluding wire shown in FIG. 1;

FIG. 15 is a partial cross-sectional side view of the occluding wire shown in FIG. 14 being inserted into the distal end of the infusion catheter shown in FIG. 13.

DETAILED DESCRIPTION OF THE PREFERRED EMBODIMENTS

Although the present invention is directed to an occluding wire that is specially adapted to provide for tactual feel during placement of the occluding wire within various types of catheters, a preferred use is in combination with an improved infusion system developed in conjunction with the occluding wire with tactual feel. Therefore, in order to understand how the tactual occluding wire functions in conjunction with the improved infusion system, a detailed discussion of the infusion system will be given. As an occluding wire is required, a guide wire equipped with an occluding ball and the tactual spring wire portion will be introduced. It should be understood that a guide wire or other wire without an occluding ball can be used in conjunction with other catheters in which an occluding ball is not required or is incompatible.

Figure 1:
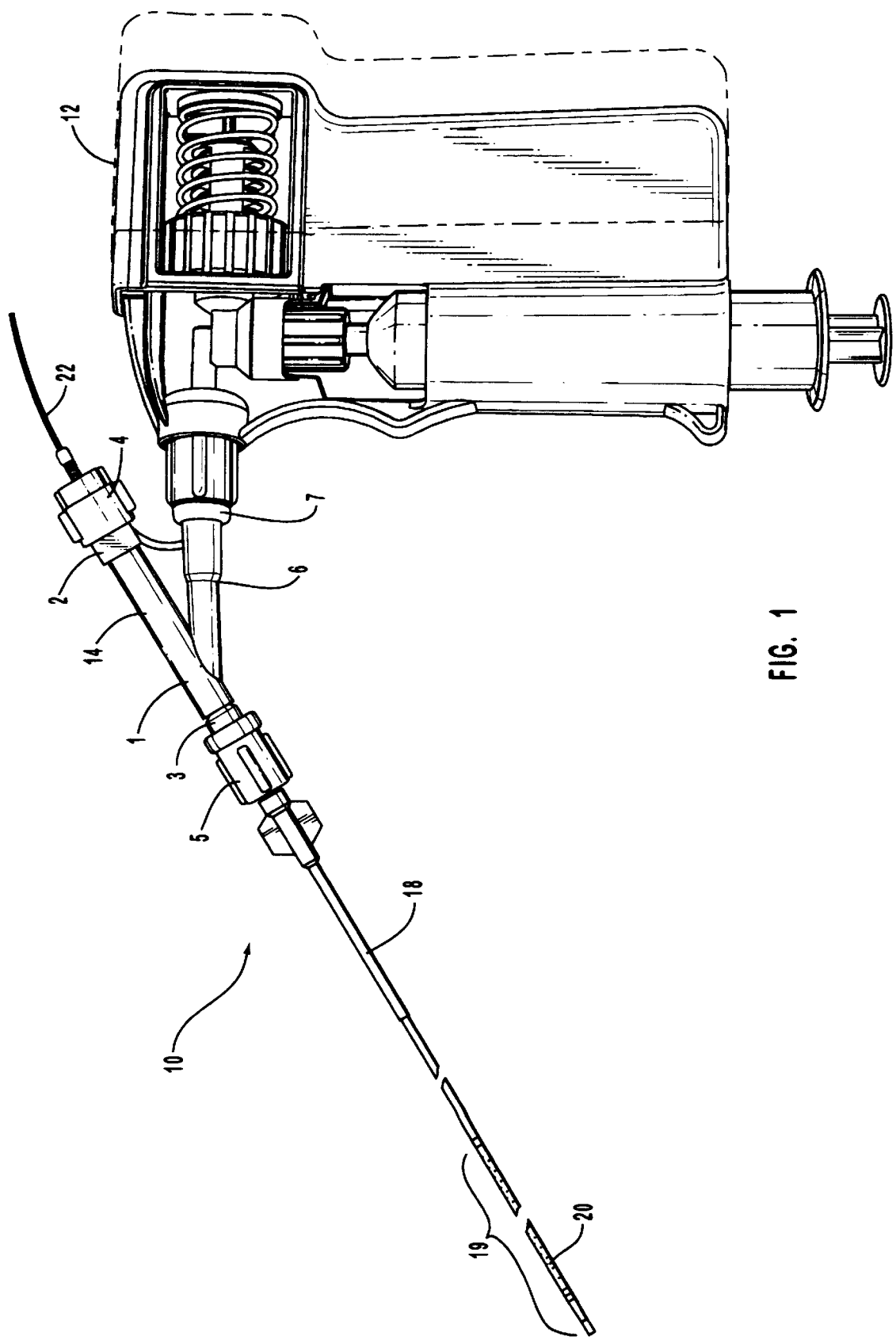
FIG. 1 is a side view of one embodiment of the inventive fluid infusion system.

Depicted in FIG. 1 is one embodiment of a fluid infusion system 10 incorporating features of the present invention. Infusion system 10 includes a three-way connector 14 having a hollow primary tube 1 extending from a proximal end 2 to a distal end 3. Positioned at proximal end 2 is a knob 4 that is rotatable to selectively close a tubular seal not shown but positioned therein. Positioned at distal end 3 is a conventional rotator connector 5. Three-way connector 14 further includes a hollow secondary tube 6 projecting from primary tube 1 in fluid communication therewith. Secondary tube 6 terminates at a threaded end 7. Three-way connector 14 can include a conventional hemostasis valves. One embodiment of a three-way hemostasis valves is further disclosed in U.S. Pat. No. 5,591,137 entitled Hemostasis Valve with Locking Seal, filed Jul. 14, 1995 in the name of Brian Stevens, which patent is incorporated herein by specific reference.

Infusion system 10 further includes a hand operated pump 12 directly fluid coupled to second tube 6 of three-way connector 14. In an alternative embodiment, a flexible tube can be used to fluid couple pump 12 to three-way connector 14. Fluid coupled to distal end 3 of three-way connector 14 is an elongated, pliable infusion catheter 18. Infusion catheter 18 has a distal end 19 with a plurality of infusion holes 20 extending therethrough.

During use, distal end 19 of infusion catheter 18 is selectively positioned within the vascular system of a patient. An occluding wire 22 is inserted into proximal end 2 of three-way connector 14 and then slidably passed through three-way connector 14 and into infusion catheter 18. Occluding wire 22 seals distal end 19 of infusion catheter 18 closed as will be discussed later in greater detail. With occluding wire 22 positioned, knob 4 is rotated on three-way connector 14 so as to seal three-way connector 14 closed around occluding wire 22. A surgeon then manually operates pump 12 so as to repeatedly pump predetermined amounts of a desired fluid into catheter 18. In turn, the fluid is forcefully discharged in small streams out through infusion holes 20 and into the vascular system.

In one use, distal end 19 of infusion catheter 18 can be positioned through or adjacent to a blood clot. The pumped fluid would be a blood clot dissolving agent such as urokinase or streptokinase. It is envisioned however, that infusion system 10 can also be used for other purposes, for example, removing fat or other deposits on the wall of a vein or artery.

The present invention includes pump means fluid coupled to the proximal end of the infusion catheter 18 for repeatedly dispensing predetermined amounts of fluid into the infusion catheter 18. By way of example and not by limitation, depicted in FIG. 2, pump 12 primarily comprises a body 30 that slidably interacts with a handle 32. Body 30 comprises a head 34 positioned at a top end 36 and a hollow finger rest 38 positioned at an opposing bottom end 40. An access opening 42 transversely extends through body 30 between head 34 and finger rest 38. Head 34 includes a valve housing 44 having a nozzle 46 and a dispensing barrel 48 positioned on opposing sides thereof. A rotator connector 47 is attached to nozzle 46. Formed on the exterior of dispensing barrel 48 are engagement threads 50. Projecting from valve housing 44 into access passageway 42 is a stem 52. Stem 52 terminates at a threaded end 54. Head 34 further includes an elongated, inverted T-shaped alignment ridge 56 positioned at top end 36 and extending over dispensing barrel 48.

Finger rest 38 has a substantially cylindrical configuration with an interior surface 57 bounding a cylindrical loading chamber 58. Loading chamber 58 longitudinally extends between access opening 42 and bottom end 40 of body 30. An upper finger grip 60 extends between nozzle 46 and loading barrel 38. A lower finger grip 61 projects from finger rest 38 at bottom end 40 and is in alignment with upper finger grip 60. Projecting from the side of finger rest 38 opposite finger grips 60 and 61 is an elongated coupling plate 62. Extending out from each side of coupling plate 62 are a plurality of spaced apart alignment ridges 64. Coupling plate 62 terminates at an outside edge 63 having a recess 68 formed thereon. A spring post 66 projects out from a recess 68 and is configured to receive a spring 67.

Figure 3:
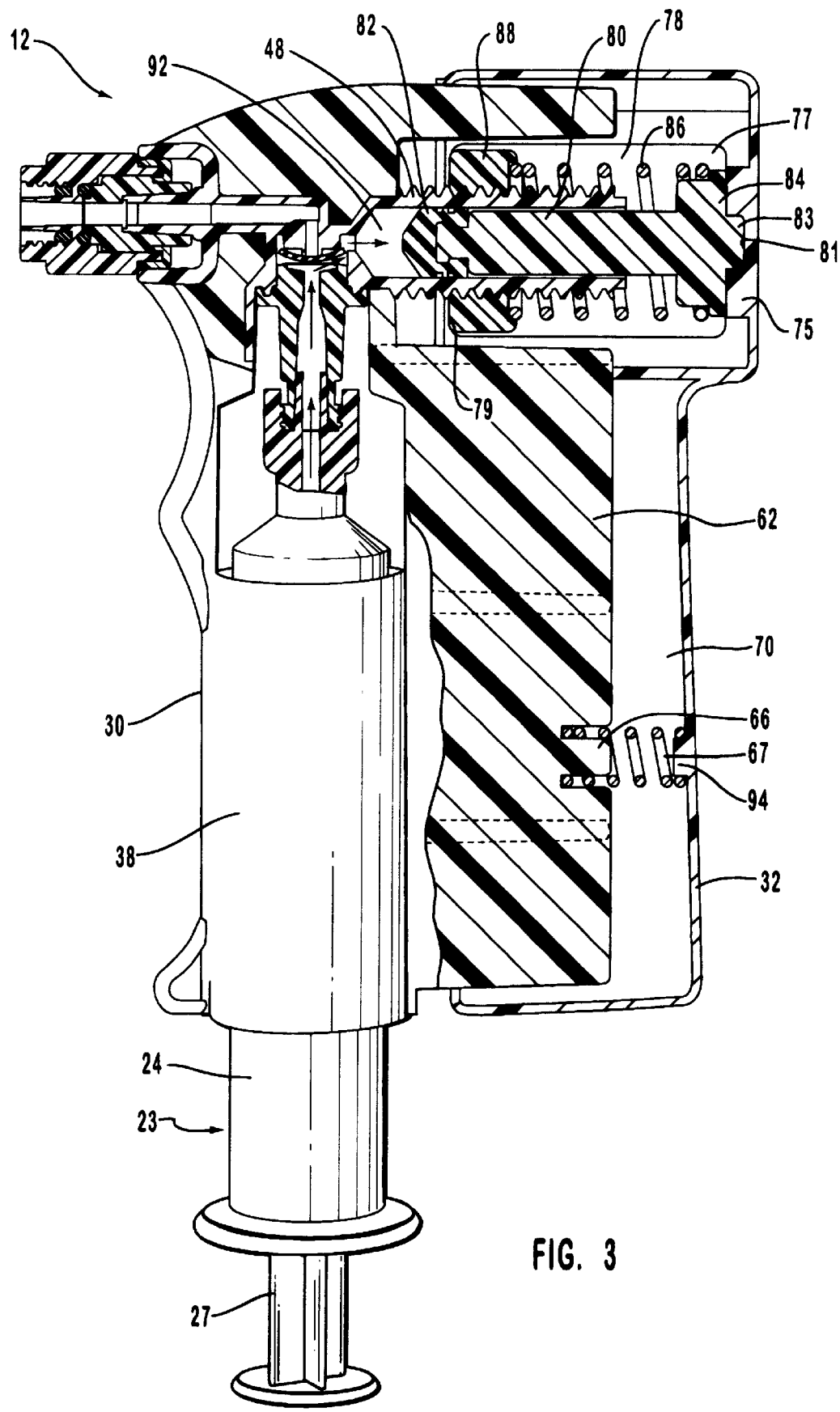
FIG. 3 is a partial cross-sectional side view of the pump shown in FIG. 2 in a first position.

The present invention also includes container means for holding a defined amount of fluid. By way of example and not by limitation, a syringe 23 is depicted having a barrel 24 with an open dispensing end 26. Positioned at dispensing end 26 is rotator connector 25. Slidably received within the opposing end of syringe 24 is a plunger 27. Finger rest 38 is used in part as a protective cover for the container means attached to pump 12. For example, once barrel 24 is fill with a desired fluid for dispensing, dispensing end 26 is slidably received within loading chamber 58 of finger rest 38 and advanced to stem 52. As a result of access opening 42, connector 25 of syringe 23 can be manually threaded onto threaded end 54 of stem 52, thereby forming a fluid connection therebetween. In this position, as depicted in FIG. 3, finger rest 38 substantially encloses syringe 23, thereby preventing syringe 23 from accidentally being bumped. Furthermore, even if syringe 23 was bumped, barrel 24 would bias against interior surface 57 of finger rest 38, thereby preventing syringe 23 from breaking off at stem 52.

Figure 2:
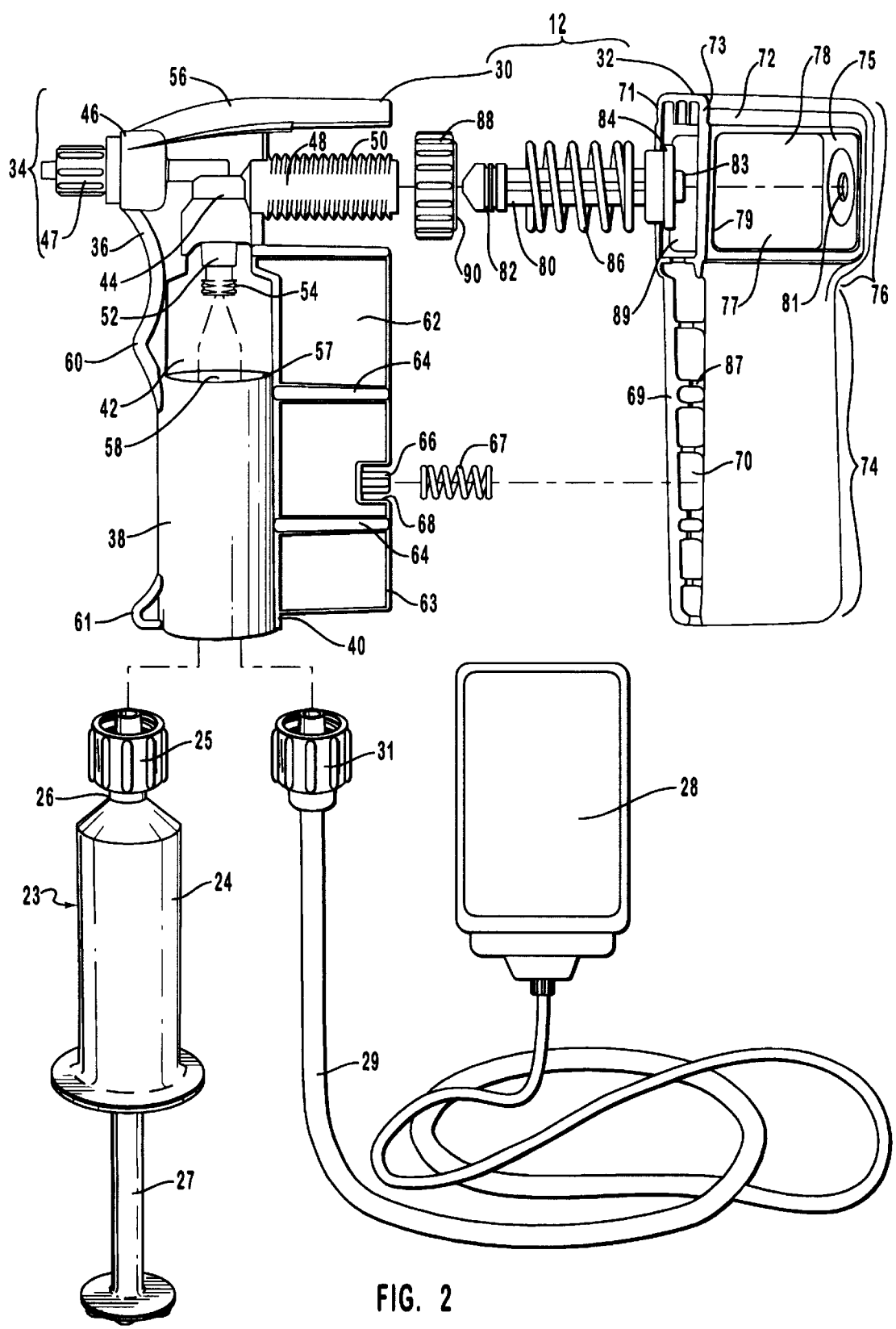
FIG. 2 is a partial side view of the pump shown in FIG. 1 in a disassembled condition with the handle thereof disposed in a perspective view.

Also depicted in FIG. 2, the container means can also include a flexible tube 29 having a fluid bag 28 attached at one end and a rotator connector 31 attached at the opposing end. Fluid bag 28 is fluid coupled to pump 12 by passing connector 31 through finger rest 38 and manually screwing to threaded end 54 of stem 52.

As depicted in FIG. 2, handle 32 has an elongated box shaped configuration that includes an elongated palm rest 74 with an enlarged plunger housing 76 mounted on the top thereof. Palm rest 74 has a front face 69 with a slot 70 extending inward and along the length thereof. Projecting into slot 70 are a plurality of guides 87. Guides 87 configure slot 70 so as to substantially complementary receive coupling plate 62 with alignment ridges 64 projecting therefrom.

Plunger housing 76 includes opposing sidewalls 71 and 72 which extend between a front face 73 and a back wall 75. Plunger housing 76 bounds a plunger chamber 77. A port 89 extends from front face 73 into plunger chamber 77. An annular recess 81 communicates with plunger chamber 77 and extends into back wall 75. A side opening 78 extends through each sidewall 71 and 72 of plunger housing 76 so as to each communicate with plunger chamber 77. Each side opening 78 is partially bounded by an inside edge 79 that is formed adjacent to and parallel with front face 73.

Pump 12 further includes a plunger 80 having an elastic tip 82 at one end and an enlarged annular flange 84 radially projecting out at the opposing end. A cylindrical post 83 projects from the opposing side of flange 84. A resiliently flexible spring 86 freely encircles plunger 80 and is configured to bias against flange 84. Finally, pump 12 also includes an annular control knob 88. Control knob 88 has a threaded aperture 90 extending therethrough. threaded aperture 90 is configured to rotatably engage threads 50 on the exterior of dispensing barrel 48.

As depicted in FIG. 3, pump 12 is assembled by initially positioning control knob 88 over tip 82 of plunger 80 and then inserting plunger 80 with spring 86 and control knob 88 into plunger chamber 77 through one of infusion holes 78. In this position, flange 84 is biased against back wall 75 with post 83 received within recess 81. Furthermore, control knob 88 is biased against the inside edge 79 of each side opening 78. Spring 86 is compressed between control knob 88 and flange 84, thereby holding plunger 80 within plunger chamber 77.

Next, tip 82 of plunger 80, projecting from plunger chamber 77, is slidably received within a barrel chamber 92 of dispensing barrel 48. Simultaneously, coupling plate 62 is slidably received within slot 70 of handle 74. Spring 67 mounted on post 66 of coupling plate 62 is also mounted on a spring post 94 positioned within palm rest 74. Control knob 88 is rotatably advanced on dispensing barrel 48, thereby securing handle 32 to body 30.

One of the unique benefits of pump 12 is that it can be operated using a single hand. During operation of pump 12, the user holds pump 12 by placing the palm of the hand against palm rest 74 and curling each of the fingers around finger grips 60 and 61 and finger rest 38. As the fingers are drawn towards the palm, springs 67 and 86 are compressed, thereby compressing body 30 against handle 32.

Figure 4:
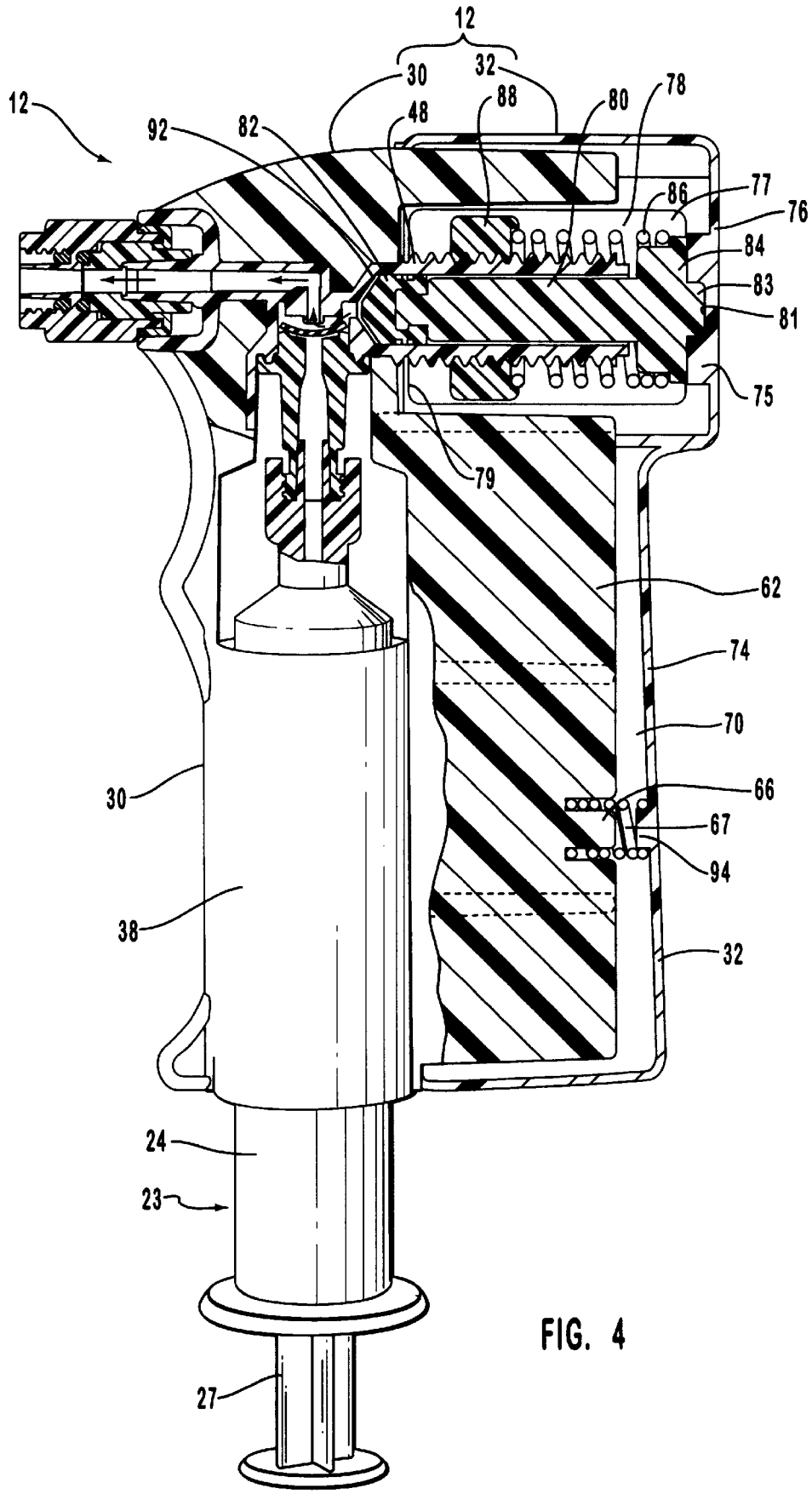
FIG. 4 is a partial cross-sectional view of the pump shown in FIG. 3 in a second position.

Plunger 12 operates between a first position and a second position. Depicted in FIG. 3, pump 12 is in the first position with body 30 and handle 32 biased apart by springs 67 and 86. In this first position, plunger 12 is retracted within barrel chamber 92. In the second position, as depicted in FIG. 4, body 30 and handle 32 are manually pressed together, thereby compressing springs 67 and 86 and advancing plunger 80 within barrel chamber 92.

The present invention also includes means for automatically retracting plunger 80 within dispensing barrel 48 after plunger 80 is manually advanced within dispensing barrel 48. By way of example and not by limitation, as the user extends the fingers curled around finger rest 38, springs 86 and 67 resiliently expand so as to automatically separate body 30 from handle 32, thereby also retracting plunger 80 within dispensing barrel 48 as discussed above. Accordingly, as an individual repeatedly squeezes and releases pump 12, plunger 80 repeatedly advances and retracts within dispensing barrel 48. There are of course a variety of alternative spring configurations that could work equally well to accomplish the retracting means. One such alternative is discussed with regard to the embodiment depicted in FIGS. 7–9. It is likewise envisioned that springs 86 and 67 could be replaced with alternative elastomeric materials such as rubber sleeves.

The present invention also includes regulating means partially mounted on the exterior surface of dispensing barrel 48 for selectively controlling how far plunger 80 can slide within dispensing barrel 48. By way of example and not by limitation, as control knob 88 is selectively advanced by rotation along the length of dispensing barrel 48, piston 80 moves to a corresponding position. For example, as control knob 88 is moved towards the free end of dispensing barrel 48, plunger 80 is correspondingly retracted within dispensing barrel 48. As a result, the volume of barrel chamber 92 unoccupied by plunger 80 is increased which, as will be discussed later, is filled with the fluid to be dispensed. Accordingly, as control knob 88 is advanced rearward, more fluid enters and is dispensed from barrel chamber 92. Conversely, as control knob 88 is advanced towards the front of dispensing barrel 48, less fluid enters and is subsequently dispensed from barrel chamber 92. Accordingly, by selectively positioning control knob 88 along dispensing barrel 48, a desired amount of fluid can be repeatedly dispensed from pump 12 at each squeezing thereof.

Figure 5:
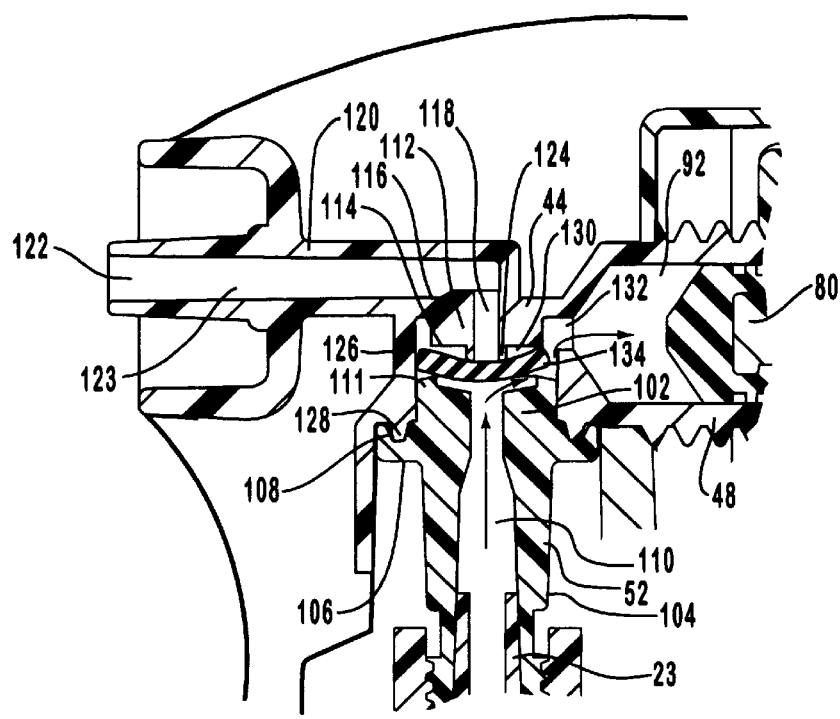
FIG. 5 is an enlarged cross-sectional side view of the valve housing of the pump shown in FIG. 3.

As depicted in FIG. 5, valve housing 44 includes a barrier wall 112 having a first side 114 and opposing second side 116 with a passageway 118 longitudinally extending therebetween. Formed on second side 116 of barrier wall 112 is a discharge tube 120 having an passageway 122 extending therethrough. Passageways 118 and 122 are in fluid communication and define an outlet passageway 123. Projecting from first side 114 of barrier wall 112 around the opening of passageway 118 is an annular sealing ring 124. An annular sidewall 126 projects down from first side 114 of barrier wall 112 around the perimeter thereof. Annular sidewall 126 terminates at an annular coupling ridge 128.

Stem 52 has an outer surface 104 extending between threaded end 54 and a top end 102. Also longitudinally extending between threaded end 54 and a top end 102 is an inlet passageway 110. Projecting from top end 102 of stem 52 around the outside edge thereof is an annular sealing lip 111. An annular flange 106 radially outwardly projects from outer surface 104. Recessed in one side of flange 106 is an annular groove 108 configured complementary to coupling ridge 128. During assembly, top end 102 of stem 52 is received within valve housing 44 such that coupling ridge 128 is received within groove 108. Coupling ridge 128 and groove 108 are secured together by an adhesive.

Extending between top end 102 of stem 52 and first side 114 of barrier wall 112 is a valve chamber 130. An opening 132 extends from valve chamber 130 to barrel chamber 92. Positioned within valve chamber 130 is a flexible, disc shaped gasket 134. In one embodiment, gasket 134 is formed from a silicone rubber. Under ambient conditions, gasket 134 is biased between sealing ring 124 and sealing ridge 111. During operation, as plunger 80 is retracted within dispensing barrel 48, a relative negative pressure is created within barrel chamber 92. As a result, fluid is sucked up from syringe 23, or some other attached fluid source, through inlet passageway 110 of stem 52 and into valve chamber 130 as depicted in FIG. 5. In turn, the outside perimeter of gasket 134 is flexed up and off of sealing lip 111 allowing the fluid to pass from valve chamber 130 and into barrel chamber 92 through opening 132. During the flow of fluid into barrel chamber 92, gasket 134 remains biased against sealing ring 124, thereby preventing fluid from passing into outlet passageway 123.

Figure 6:
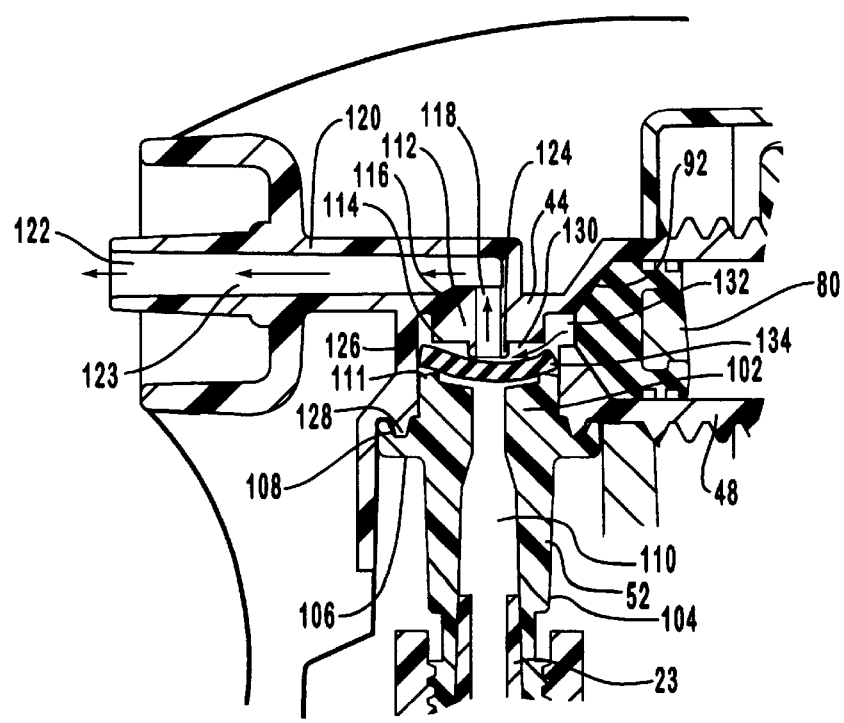
FIG. 6 is an enlarged cross-sectional side view of the valve housing of the pump shown in FIG. 4.

As depicted in FIG. 6, as plunger 80 is advanced within dispensing barrel 48, fluid within barrel chamber 92 is pushed through opening 132 into valve chamber 130. As a result of the direction of the fluid flow, gasket 134 bulges down and away from sealing ring 124 allowing fluid into outlet passageway 123. During this fluid flow, gasket 134 remains pressed against sealing ridge 111, thereby preventing the fluid from passing into inlet passageway 110 of stem 52.

The present invention also includes valve means positioned within valve housing 44 for enabling fluid to pass from inlet passageway 110 to dispensing barrel 48 when plunger 80 is retracted within barrel 48 and for enabling fluid to pass from dispensing barrel 48 to outlet passageway 123 when plunger 80 is advanced within dispensing barrel 48. One example of the valve means includes gasket 134 interacting with valve chamber 130 as discussed above. Further disclosure with regard to the above valve assembly and alternatives thereto are found in U.S. patent application Ser. No. 09/198,608 entitled Check Relief Valve, filed Feb. 18, 1994 in the names of Mark A Christensen and Arlin D.

Nelson (now abandoned), which is incorporated herein by specific reference.

In one embodiment of the present invention, the components of pump 12 are injection molded from a plastic. In the preferred embodiment, body 30 is comprised of polycarbonate. In contrast, handle 32 and plunger 80 are comprised of ABS (Acrylonitrile Butadiene Styrene). By making the above elements out of different materials, the elements more easily slide together.

Figure 7:
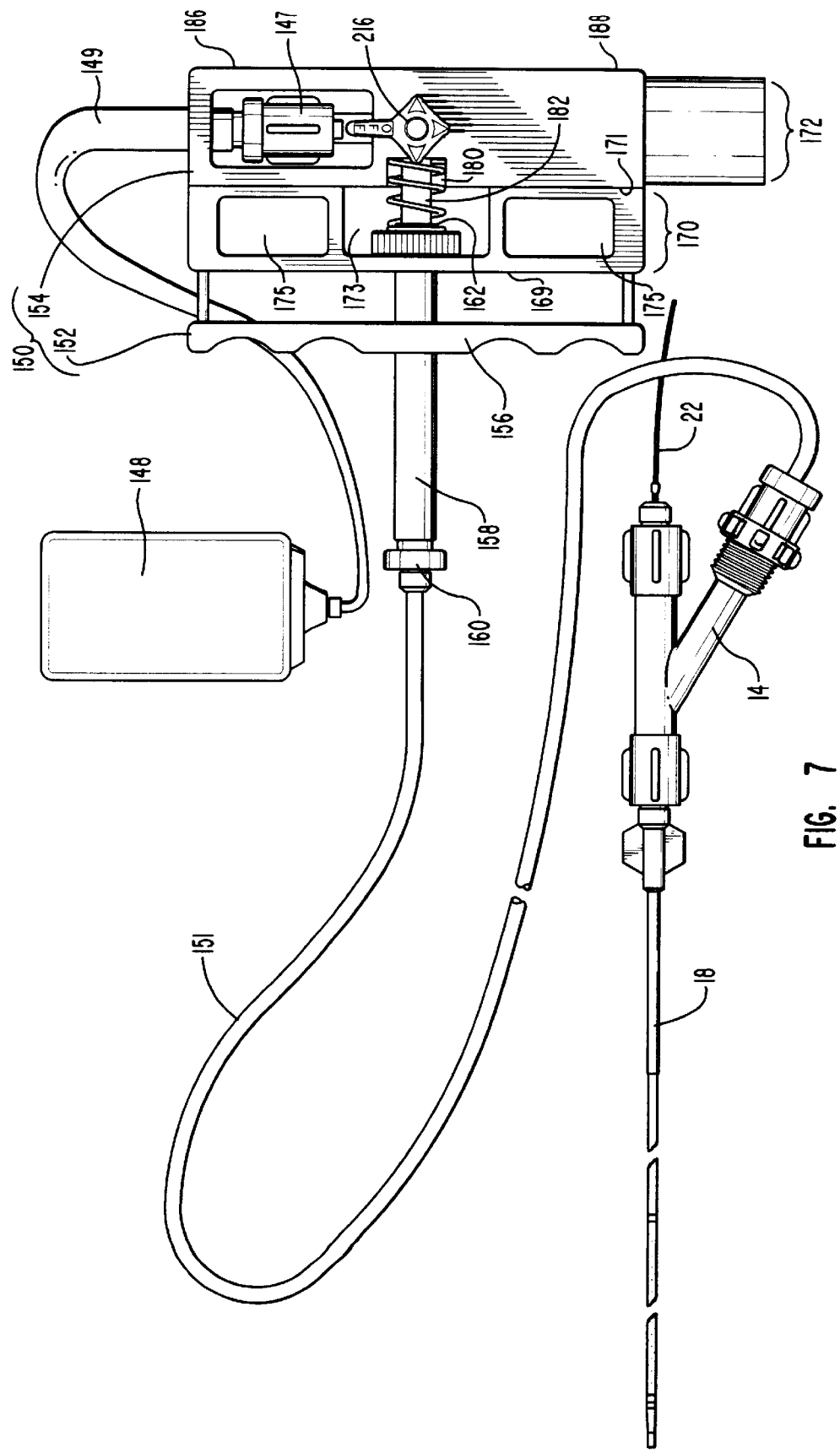
FIG. 7 is a side view of an alternative embodiment of a fluid infusion system.

Depicted in FIG. 7 is an alternative embodiment of a pump 150 for use in dispensing a fluid into infusion catheter 18 through three-way connector 14. Pump 150 is depicted as being fluid coupled to three-way connector 14 by way of a flexible tube 151. In alternative embodiments, pump 150 can be directly connected to three-way connector 14. As will be discussed later in greater detail, pump 150 can be fluid coupled to an external fluid source, such as fluid bag 148, by way of a flexible tube 149 having a rotator connector 147 mounted on the end thereof.

Pump 150 comprises a body 152 that is slidably mounted against a handle 154. Body 152 includes an elongated finger rest 156 with an elongated barrel 158 extending therethrough. Barrel 158 has a distal end 159 (see FIG. 8) with a rotator connector 160 attached thereto and an opposing threaded proximal end 162. Body 154 includes a relatively thin, substantially rectangular front support 170 having a front edge 169 and a rear edge 171. A plunger chamber 173 transversely extends through front support 170. Side apertures 175 transversely extend through front support 170 on each side of plunger chamber 173.

Figure 8:
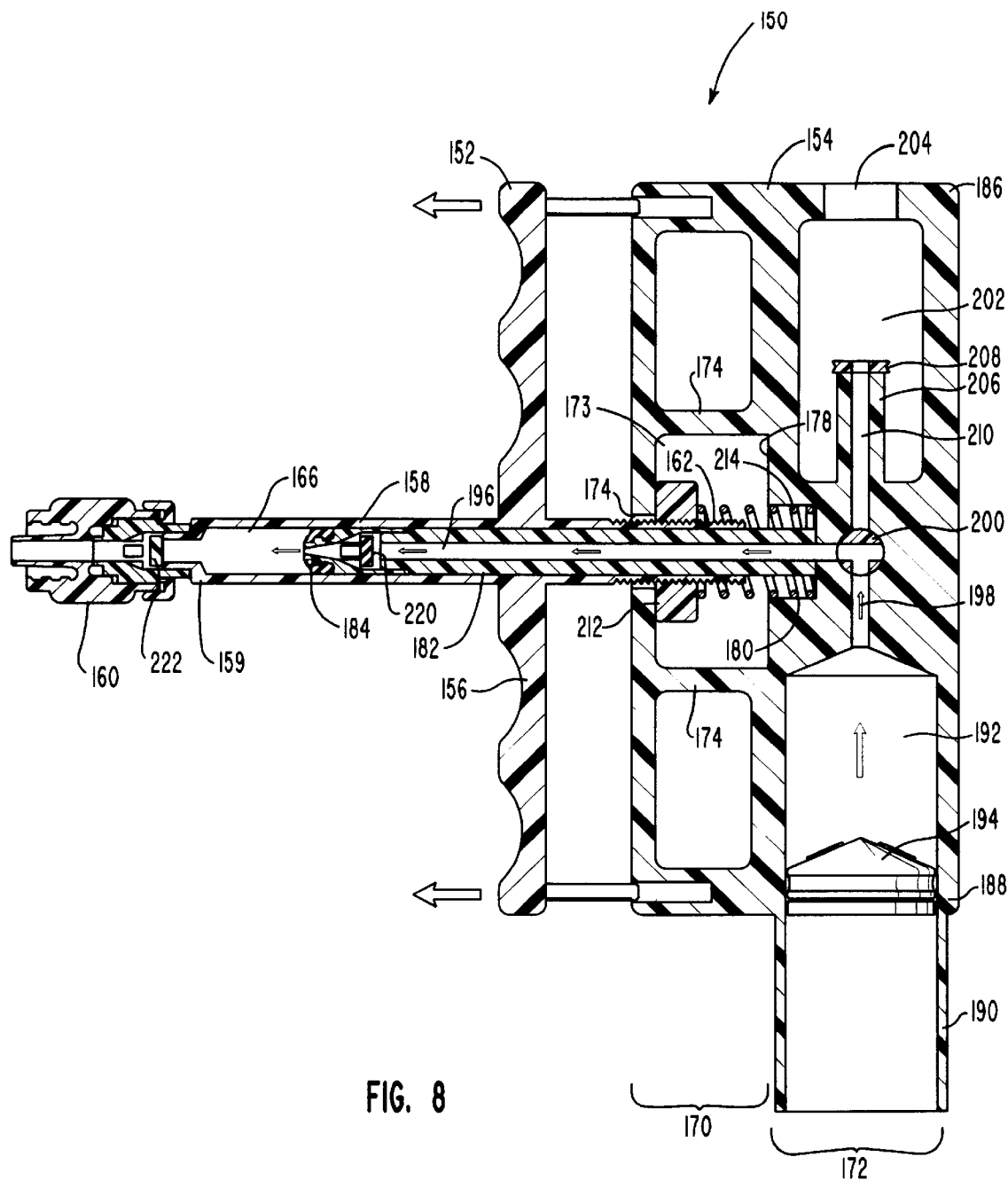
FIG. 8 is a cross-sectional side view of the pump shown in FIG. 7 in a first position.

Body 154 further includes a substantially cylindrical palm rest 172 mounted to rear edge 171 of front support 170. A spring recess 180 extends into palm rest 172 in alignment with front support 170. Projecting from spring recess 180 is an annular plunger 182. As depicted in FIG. 8, plunger 182 terminates at a sealing tip 184 and is slidably received within a barrel chamber 166 of barrel 158. Longitudinally extending from tip 184 of plunger 182 to a junction 200 (see FIG. 8) within palm rest 172 is a plunger passageway 196. A rotatable cock valve 216 is positioned at junction 200.

Palm rest 172 extends between a top end 186 and an opposing base end 188. Projecting from base end 188 is an annular extension sleeve 190. A cylindrical fluid reservoir extends through sleeve 190 and into base end 188 of palm rest 172. Slidably positioned with fluid reservoir 192 is a seal 194. A first passageway 198 extends from fluid reservoir 192 to junction 200, thereby enabling select fluid coupling between first passageway 198 and plunger passageway 196.

Transversely extending through palm rest 172 at top end 186 is an access opening 202. Extending through top end 186 into access opening 202 is an aperture 204. Projecting into access opening 202 opposite aperture 204 is a stem 206. Stem 206 terminates at a threaded end 208. A second passageway 210 longitudinally extends through stem 206 to junction 200, thereby enabling select fluid coupling between second passageway 210 and plunger passageway 196.

During assembly, proximal end 162 of barrel 158 is slidably received within a port 174 extending from front edge 169 of front support 170 to plunger chamber 173. A threaded control knob 212 is threadedly engaged on proximal end 162 of barrel 158. Control knob 212 has an outside diameter smaller than the inside diameter of port 174, thereby preventing separation of body 152 from handle 154. A resiliently compressible spring 214 has a first end disposed within spring recess 180 and an opposing second end continually biased against control knob 212. Under ambient conditions, spring 214 continually urges control knob 212 against front support 170.

Figure 9:
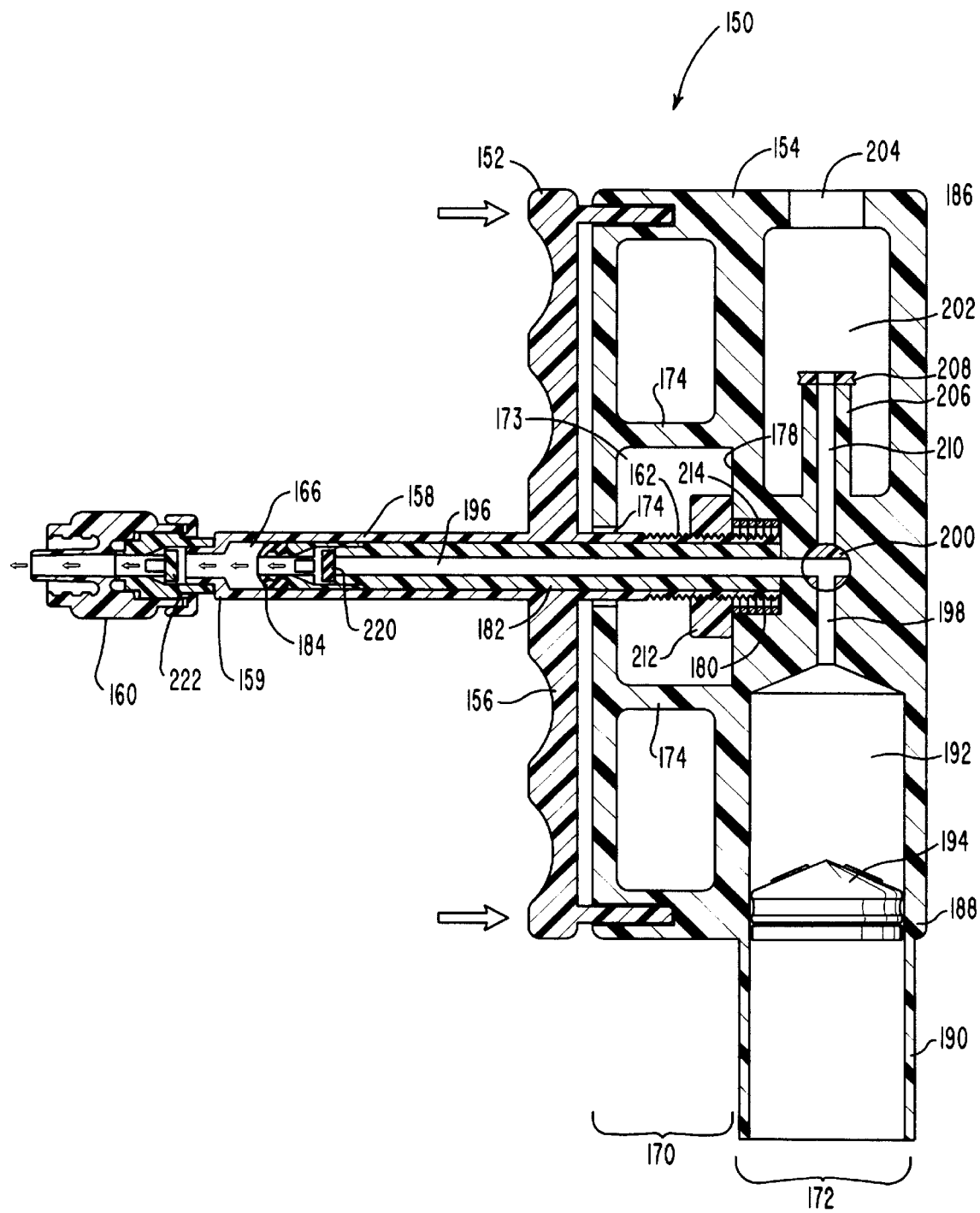
FIG. 9 is a cross-sectional side view of the pump shown in FIG. 8 in a second position.

During use, the user places the palm of the hand against palm rest 172 with the finger wrapped around finger rest 156. Pump 150 operates between a first position and a second position. Depicted in FIG. 8, pump 150 is in the first position. As shown therein, spring 214 biases body 152 and handle 154 apart, thereby retracting plunger 182 within barrel 158. As the fingers wrapped around finger rest 156 are drawn back towards to the users palm, spring 214 is compressed as body 152 and handle 154 are drawn together, thereby moving pump 150 into the second position as depicted in FIG. 9. As body 152 and handle 154 are drawn together, plunger 182 is advanced within barrel chamber 166.

As the users fingers are released, spring 214 automatically separates body 152 and handle 154, thereby forcing the retraction of plunger 182 within barrel chamber 166. Accordingly, plunger 182 can be repeatedly advanced and retracted within barrel chamber 166 by the user repeatedly squeezing and releasing pump 150. Control knob 212 selectively controls how far plunger 182 can advance within barrel chamber 166. Accordingly, by selectively positioning control knob 212, a desired amount of fluid is repeatedly dispensed from pump 150.

Figure 10A:
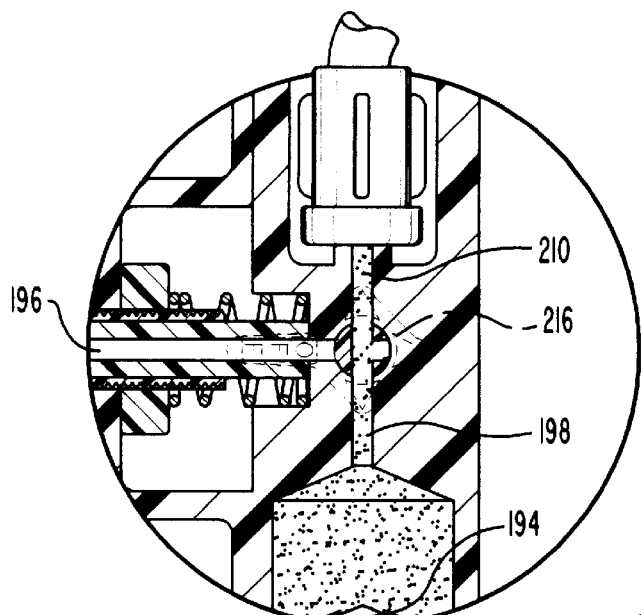
FIGS. 10A–10C are cross-sectional side views of the pump handle shown in FIG. 6 with the cock valve thereon moved to three separate positions.
Figure 10B:
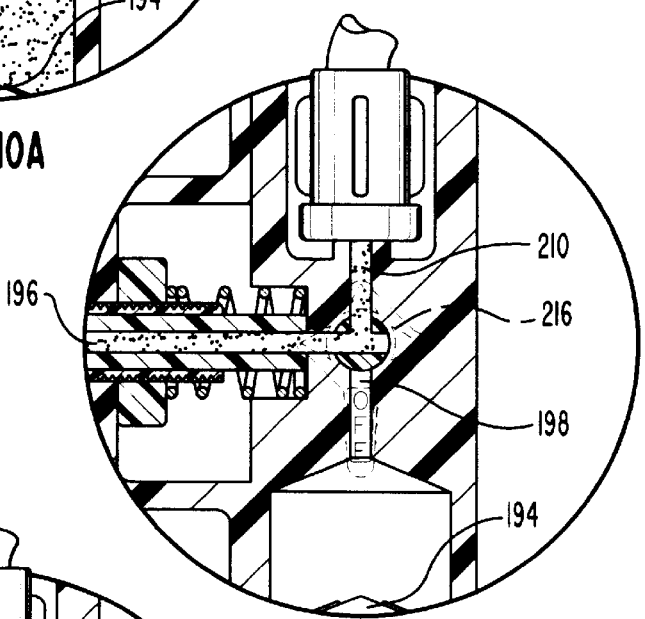
Figure 10C:
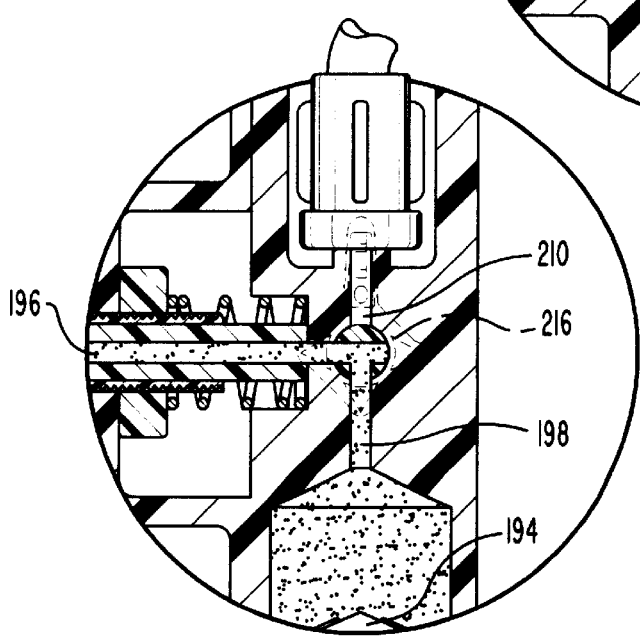

As depicted in FIGS. 10A–10C, check valve 216 can be selectively positioned to facilitate desired communications between first passageway 198, second passageway 210, and plunger passageway 196. For example, depicted in FIG. 10A check valve 216 is positioned to facilitate isolated fluid communication between first passageway 198 and second passageway 210. In this position, a fluid source can be secured to threaded end 208 (see FIG. 9) of stem 206 (see FIG. 9) so as to selectively fill fluid reservoir 192 (see FIG. 9). As fluid reservoir 192 is filled, seal 194 automatically slides towards the end of sleeve 190.

Depicted in FIG. 10B, check valve 216 is rotated to facilitate isolated fluid communication between second fluid passageway 210 and plunger passageway 196. In this configuration, fluid can be dispensed by pump 150 through a fluid source attached to stem 206. Alternatively, as depicted in FIG. 10C, check valve 216 is positioned to effect isolated fluid communication between first passageway 198 and plunger passageway 196. In this configuration, pump 150 dispenses fluid from fluid reservoir 192. As fluid is drawn from fluid reservoir 192, seal 194 automatically slides towards first passageway 198.

Figure 11A:
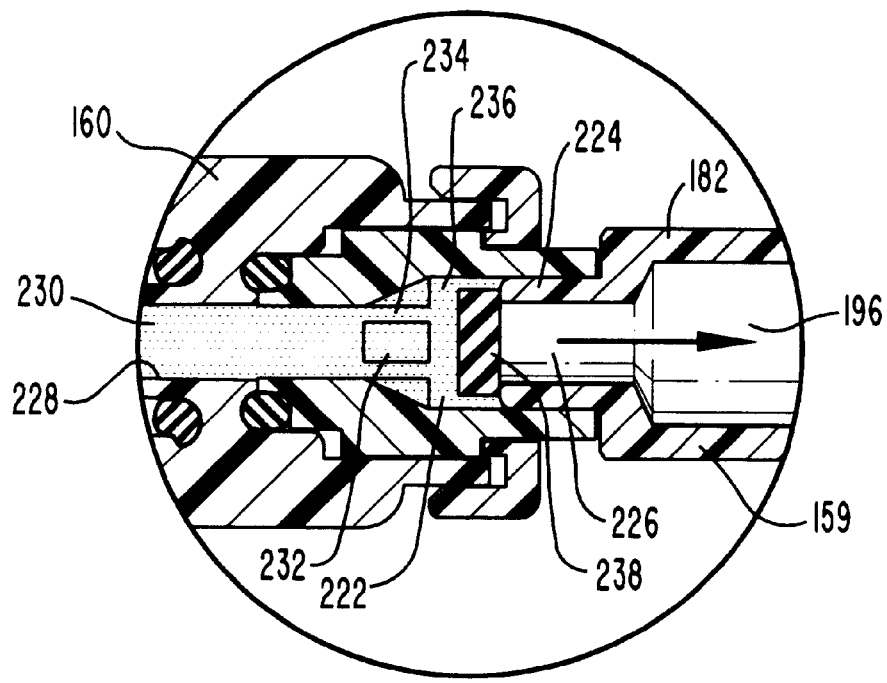
FIG. 11A is a cross-sectional side view of the second check valve shown in the barrel of the pump as shown in FIG. 8.
Figure 11B:
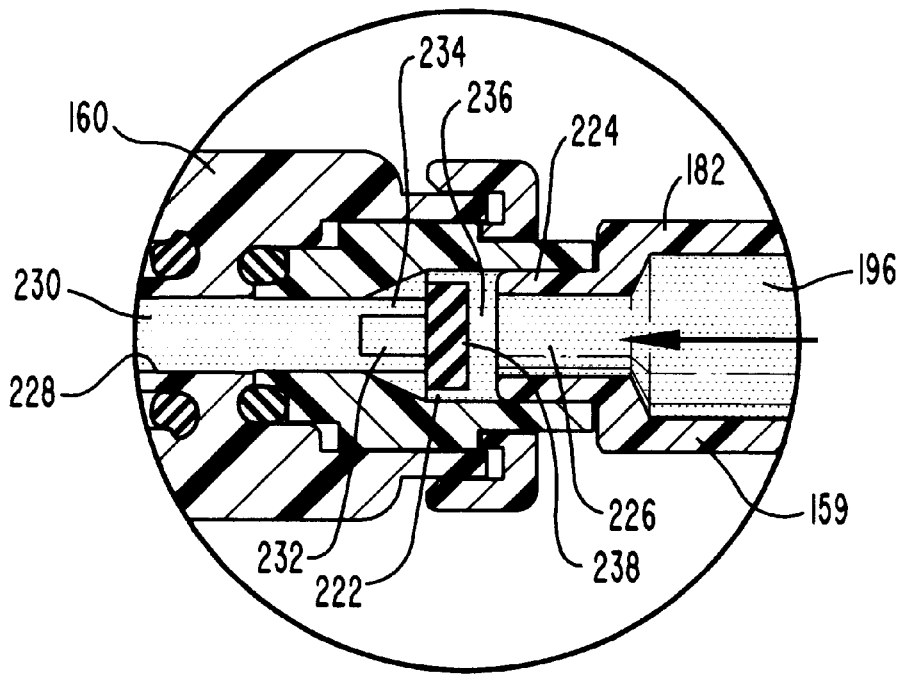
FIG. 11B is a cross-sectional side view of the second check valve shown in the barrel of the pump as shown in FIG. 9.

Fluid is advanced through pump 150 as a result of the interaction between two check valves. As depicted in FIG. 8, a first check valve 220 is positioned in plunger passageway 196 at the tip of plunger 182. A second check valve 222 is positioned between the tip of barrel 158 and rotator connector 160. Depicted in FIGS. 11A and 11B is an enlarged cross-sectional view of second check valve 222. Second check valve 222 is shown as comprising a cylindrical sleeve 224 projecting from distal end 159 of barrel 182. A valve passageway 226 extends through sleeve 224 and communicates with barrel chamber 196. Rotator connector 160 is secured by an adhesive to the exterior of sleeve 224. Rotator connector 160 has an interior surface 228 bounding a passageway 230 extending therethrough. Radially inwardly projecting from interior surface 228 of rotator connector 160 at a distance from sleeve 224 are a plurality of spaced apart retention shelves 232. Channels 234 extend between each retention shelf 232. Positioned between shelves 232 and sleeve 224 is an enlarged valve chamber 236. Freely housed within valve chamber 236 is a disk shaped gasket 238.

First check valve 220 has substantially the same structural elements as second check valve 222. Accordingly, like structural elements between first check valve 220 and second check valve 222 are identified by like reference characters.

During operation, as plunger 182 is advanced within barrel 158, as previously discussed, fluid within barrel chamber 166 pushes gasket 238 of first check valve 220 against shelves 224 as depicted in FIG. 8, thereby closing fluid communication between barrel chamber 166 and plunger passageway 196. Simultaneously, the fluid pushes gasket 238 of second check valve 222 against retention shelves 232, thereby allowing the fluid within barrel chamber 166 to pass around gasket 238, through channels 234, and out pump 150.

As plunger 182 is retracted within barrel 158 a relative negative pressure is produced within barrel chamber 196. As a result, gasket 238 of second check valve 222 seals against sleeve 224, as depicted in FIGS. 9 and 11A. Simultaneously, gasket 238 of first check valve 220 is biased against retention shelves 232. The relative negative pressure created within barrel chamber 166 causes fluid to be drawn from either first passageway 198 or second passageway 210, depending on the position of stop cock 220, such that fluid passes down plunger passageway 196 and into barrel chamber 166. Once plunger 182 is fully retracted, plunger 182 can again be selectively advanced to dispel the fluid within barrel chamber 196. Accordingly, by repeatedly squeezing pump 150, fluid is repeatedly dispersed in desired predetermined amounts.

Depicted in FIG. 12, infusion catheter 18 has a body wall 250 longitudinally extending between a proximal end 252 and an opposing distal end 254. In one embodiment, infusion catheter 18 is formed from a nylon having a durometer of about shore 70D. Attached at proximal end 252 is a winged connector 256 having a threaded end 258. An outer sleeve 260 covers proximal end 252 of catheter 18 to help prevent kinking of body wall 250. Distal end 254 of catheter 18 includes a infusion length 261. Infusion length 261 has a plurality of infusion holes 20 extending therethrough, preferably in a double spiral configuration.

Individual infusion holes 20 are preferably spaced along infusion length 261 at regular intervals; for example, at intervals of about 0.050 inch. Infusion holes 20 are grouped together in sets of four holes radially spaced apart at 90° intervals. Each succeeding set of four holes is preferably rotated relative to the immediately proceeding set of four holes by about 18° in order to create a staggered hole arrangement that results in a more diverse spray pattern.

Thus, in a preferred embodiment, the second infusion hole will be radially spaced at an interval of 90° relative to the first infusion hole, the third infusion hole will be radially spaced 180° with respect to the first infusion hole, while the fourth infusion hole will be radially spaced 270° with respect to the first infusion hole. However, rather than being spaced at 360° (or 0°) relative to the first hole, the fifth infusion hole will begin a new group of four holes and be radially spaced from the first infusion hole by some amount between 1° and 89°, most preferably about 18°, since this value divides evenly into the 360° (and 90°) so that a very regular yet well spaced arrangement of holes can be attained.

Thereafter, the sixth, seventh and eighth holes will be radially spaced at 90° intervals relative to each other as in the first set of four holes. The ninth hole will begin the third set of four holes and will be offset from the fifth hole by, e.g., about 18° and the first hole by about 36°. This pattern repeats itself substantially regularly along the entire infusion length of the catheter. Other angles that divide evenly into 360°, but not necessarily 90° or 180° may also be used depending on the desired spray pattern. In addition, angles that do not divide evenly into 360° may be used in order to yield an even more randomized spray pattern.

Infusion length 261 can vary between about 5 cm to about 30 cm., with diminishing hole size as the number of holes is increased. The size of each infusion hole 20 will generally range between about 0.002"–0.006". Nevertheless, the size of catheter 18 and each infusion hole 20 can be altered, as can be the longitudinal spacing between holes 20, depending on the intended use of catheter 18.

The double spiral configuration of the present invention provides a significantly improved radial dispersion of thrombolytic fluid around the circumference of catheter 18. The result is a more quickly and completely lysed blood clot using a reduced amount of thrombolytic fluid, which greatly contributes to the recovery and well-being of the patient. Further disclosure with regard to the size and patterning of infusion holes 20 is found in U.S. patent application Ser. No. 08/949,893 entitled "Catheter with Improved Spray Pattern for Pharmaco-Mechanical Thrombolysis Therapy", and filed Oct. 14, 1997 in the names of Jim D. Mottola, Stephen W. Carlstrom, and Andy E. Poursaid, which is incorporated herein by specific reference.

Encircling body wall 250 at opposing ends of infusion length 261 is a first radiopaque band 262 and a second radiopaque band 264. Catheter 18 terminates at a tapered tip 266. As depicted in FIG. 13, body wall 250 has an interior surface 268 that bounds a lumen 270 longitudinally extending between proximal end 252 and distal end 254. Lumen 270 exits catheter 18 at tip 266 through a tip opening 278. Infusion holes 20 extend through body wall 250 to communicate with lumen 270. Interior surface 268 includes a cylindrical first portion having a diameter $D_1$ extending from proximal end 252 and a cylindrical second portion 274 having a diameter $D_2$ positioned at tip 266, Diameter $D_1$ being larger than diameter $D_2$. Interior surface 268 also includes an annular, sloped taper portion 272 extending between first portion 271 and second portion 274. Radially inwardly projecting from interior surface 268 at tip opening 278 is an annular sensing ridge 276. Sensing ridge 276 has an inside diameter $D_3$.

In conjunction with the aforementioned infusion system, it is preferable to employ an occluding wire with an occluding ball and coiled spring wire for tactile feel during placement of the occluding wire within catheter 18. Although the wire discussed hereinafter is equipped with an occluding ball in order to seal catheter 18, it should be understood that, e.g., guide wires with tactual feel for use with other catheters, wherein the occluding ball is omitted as being unnecessary and/or incompatible, are within the scope of the present invention.

Depicted in FIG. 14, an occluding wire 22 has a proximal end 282 and an opposing distal end 284. Positioned at proximal end 282 is an elongated positioning wire 286. Positioning wire 286 includes a cylindrical portion 287 having a diameter $D_4$ and a sloped tapered portion 288 projecting from the end thereof. Mounted on the end of tapered portion 288 is an enlarged substantially cylindrical occluding ball 290. Projecting from occluding ball 290 on the side opposite of tapered portion 288 is a flexible, coiled spring wire 292. Spring wire 292 has a maximum outer diameter $D_5$ and terminates at a smooth cap 294. As a result of spring wire 292 being formed in a coil, the wire forms a continuously encircling ridge 295 having a continuously encircling groove 296 formed between each of the coils.

The encircling ridge 295 and encircling groove 296 of coiled spring wire 292 interact with annular sensing ridge 276 at the end of catheter 18 during insertion of occluding wire into catheter 18 to provide sensing means for allowing the user to tactually feel when the occluding wire 292 is near the end of catheter 18.

By way of example and not by limitation, listed below is one typical set of dimensions for the above discussed diameters. The measurements given below are in inches:

D1=0.048±0.0015

D2=0.036±0.0005

D3=0.033±0.0005

D4=0.015±0.0005

D5=0.035−0.0015

Infusion catheter 18 can be directly inserted into the vascular system or placed using an introducer sheath. Typically, however, catheter 18 is positioned by first inserting a guide wire into the vascular system of the body of a patient. With the guide wire appropriately positioned, infusion catheter 18 is slid over the guide wire and fed to the distal end of the guide wire. The guide wire is then removed such that infusion catheter remains in the vascular system.

Proximal end 252 of infusion catheter 18 is next coupled with three-way connector 14 and a select pump. Prior to pumping the fluid into infusion catheter 18, however, tip opening 278 must first be occluded. This is accomplished by advancing distal end 284 of occluding wire 22 into lumen 270 of catheter 18. As depicted in FIG. 15, occluding wire 18 is advanced until occluding ball 290 is seated and sealed against tapered portion 272. In this position, fluid can be pumped into lumen 270 for dispensing out through infusion holes 20.

In one embodiment of the present infusion system, sensing means are provided for tactually sensing when distal end 284 of occluding wire 22 is adjacent to tip opening 278 of catheter 18. By way of example and not by limitation, diameter $D_3$ of sensing ridge 276 is smaller than diameter $D_5$ of spring wire 292. Accordingly, as spring wire 292 passes through sensing ridge 276, sensing ridge 276 vibrates over the discrete coils of spring wire 292. A surgeon is able to tactually feel these vibrations through both occluding wire 22 and catheter 18. By sensing these vibrations, the surgeon is able to determine when occluding ball 290 is approaching seat 272. This warns the surgeon to carefully advance occluding wire 22 so that occluding ball 290 is not pushed through tip opening 278.

The present invention also includes means formed on the interior surface of the infusion catheter 18 for rubbing against spring wire 292 so as to transmit vibrations along occluding wire 22 when occluding wire 22 is advanced within the lumen of infusion catheter 18. By way of example and not by limitation, the means for rubbing against spring wire 292 comprises annular sensing ridge 276. In alternative embodiment, sensing ridge 276 need not be annular but could comprise one or more fingers inwardly projecting from the interior surface 268 of catheter 18. Furthermore, sensing ridge 276 need not be positioned at tip opening 278 but could be positioned at one or more alternative locations along the length of catheter 18.

Means mounted on occluding wire 22 are also provided for rubbing against the sensing ridge 276 so as to transmit vibrations along the occluding wire 22 when occluding wire 22 is advanced within the lumen of infusion catheter 18. By way of example, the means for rubbing against sensing ridge 276 comprises spring wire 292 as described above. In alternative embodiments, a non-coiled wire having ridges projecting therefrom would also work.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A catheter system comprising:

a body wall with an interior surface bounding a lumen, the lumen extending from a proximal end to an opposing distal end and said body wall defining a seat adjacent a tip opening located at said distal end;

a sensing ridge radially inwardly projecting from the interior surface of the body wall; and a wire with an occluding ball for forming a fluid tight seal when situated within said seat, said wire comprising a spring wire which activates a vibration for tactile sensing.

2. A catheter system as recited in claim 1, wherein the sensing ridge is located adjacent the distal end of the catheter.

3. A catheter system as recited in claim 1, wherein the catheter includes a plurality of sensing ridges disposed at desired locations along the interior surface of the body wall.

4. A catheter system as recited in claim 1, wherein the sensing ridge is substantially annular.

5. A catheter system as recited in claim 1, wherein the sensing ridge is positioned adjacent the tip opening at the distal end of the catheter.

6. A catheter system as recited in claim 1, further comprising a plurality of infusion holes extending through the body wall.

7. A catheter system as recited in claim 6, wherein the infusion holes have a diameter in a range from about 0.002 inches to about 0.006 inches.

8. A catheter system as recited in claim 6, wherein the infusion holes have a double spiral configuration.

9. A catheter system as recited in claim 1, wherein the interior surface further comprises:

(a) a substantially cylindrical first portion extending from the proximal end toward the distal end of the catheter and having an inner diameter;

(b) a second portion having a tip opening positioned adjacent the distal end of the catheter, the second portion having an average inner diameter smaller than the inner diameter of the first cylindrical portion, wherein the sensing ridge inwardly projects from the second portion; and (c) a transition portion defining a boundary between the first portion and the second portion.

10. A catheter system as recited in claim 9, wherein the second portion is substantially cylindrical and wherein the transition portion is sloped.

11. A catheter system comprising:

(a) a catheter having a body wall with an interior surface bounding a lumen, the lumen extending from a proximal end to a tip opening at an opposing distal end and said body wall defining a seat adjacent a tip opening located at said distal end;

(b) a thin elongated wire having a proximal end and an opposing distal end, the wire being configured to be received within the lumen of the catheter and having an occluding ball for forming a fluid tight seal when situated within said seat; and (c) sensing means for enabling tactile determination of when the occluding ball of said wire is nearing the seat adjacent the tip opening.

12. A catheter system as recited in claim 11, wherein the sensing means comprises:

(a) a coiled spring wire projecting from the distal end of the placement wire and having an outer diameter; and (b) an annular sensing ridge radially inwardly projecting from the interior surface of the lumen adjacent the tip opening, the sensing ridge having an inner diameter smaller than the outer diameter of the spring wire, thereby causing the sensing ridge to vibrate over the spring wire when the spring wire passes by the sensing ridge.

13. A catheter system as recited in claim 1, wherein the interior surface of the catheter comprises:

(a) a substantially cylindrical first portion extending from the proximal end toward the distal end and having an inner diameter;

(b) a second portion positioned adjacent the distal end and having a sloped portion having an inner diameter smaller than the inner diameter of the first portion.

14. A catheter system as recited in claim 13, wherein the sloped portion defines a transition portion between the substantially cylindrical first portion and the second portion.

15. A catheter system as recited in claim 13, wherein the occluding ball is configured to seal against the sloped portion within the second portion of the catheter when the wire is positioned within the catheter.

16. A catheter system as recited in claim 11, further comprising a plurality of infusion holes extending through the body wall to the lumen, the infusion holes each having a diameter smaller than the tip opening.

17. A catheter system comprising:

(a) an infusion catheter having a body wall with an interior surface bounding a lumen, the lumen extending from a proximal end to a tip opening at an opposing distal end, and a plurality of infusion holes extending through the body wall to the lumen adjacent the distal end;

(b) an occluding wire comprising a thin elongated placement wire and having an enlarged occluding ball positioned at an end thereof, wherein a coiled spring wire projects from the occluding ball remote from the placement wire; and (c) means formed on the interior surface of the infusion catheter for tactually engaging the spring wire as the occluding wire is advanced through the catheter so as to transmit vibrations along the occluding wire.

18. A catheter system as recited in claim 17, wherein the means for engaging the spring wire comprises a sensing ridge projecting radially inward from the interior surface of the infusion catheter.

19. A catheter system as recited in claim 17, wherein the sensing ridge is annular and has an inner diameter smaller than the maximum outer diameter of the spring wire.

20. A catheter as recited in claim 19, wherein the interior surface of the catheter comprises:

(a) a first portion extending from the proximal end toward the distal end and having an inner diameter;

(b) a second portion positioned adjacent the distal end and having an inner diameter smaller than the inner diameter of the first portion, the sensing ridge projecting from the second portion; and (c) an annular transition portion extending between the first portion and the second portion.

21. A catheter system comprising:

(a) an infusion catheter having a body wall with an interior surface bounding a lumen extending between a proximal end and a distal end, the interior surface including:

(i) a substantially cylindrical first portion extending from the proximal end toward the distal end, the first portion having a plurality of infusion holes extending therethrough;

(ii) a substantially cylindrical second portion positioned adjacent the distal end and terminating at a tip opening, the second portion having an inner diameter smaller than the inner diameter of the first portion; and (iii) a sloped transition portion extending between the first portion and the second portion;

(b) a sensing ridge inwardly projecting from the second portion of the interior surface of the infusion catheter;

(c) an occluding wire comprising a thin elongated placement wire having an enlarged occluding ball and a spring wire positioned at the end thereof; and (d) means formed on the interior surface of the infusion catheter for tactually engaging the spring wire as the occluding wire is advanced through the catheter so as to transmit vibrations along the occluding wire.

22. A catheter system as recited in claim 21, wherein the means for tactually engaging the sensing ridge comprises a coiled spring wire projecting from an end of the occluding ball on a side thereof opposite the positioning wire, the spring wire having a maximum outer diameter larger than the inner diameter of the lumen at the sensing ridge.

* * * * *

UNITED STATES PATENT AND TRADEMARK OFFICE
CERTIFICATE OF CORRECTION

PATENT NO. : 6,059,759
DATED : May 9, 2000
INVENTOR(S) : Jim D. Mottola, Joseph E. Biche, Stephen W. Carlstrom, Darwin L. Mullins It is certified that error appears in the above-identified patent and that said Letters Patent is hereby corrected as shown below:

Col. 5, ln. 12: after "hemostasis" change "valves" to --valve--

Col. 5, ln. 13: after "hemostasis" change "valves" to --valve--

Col. 6, ln. 19: after "24 is" change "fill" to --filled--

Col. 8, ln. 7: after "having" change "an" to --a--

Col. 13, ln. 16: after "0.035" and before "0.0015" change "-" to --±--

Col. 15, ln. 18: after "claim" change "1" to --11--

Signed and Sealed this

Tenth Day of April, 2001

*Attest:*

NICHOLAS P. GODICI

*Attesting Officer*  *Acting Director of the United States Patent and Trademark Office*